US00PP28472P2

(12) United States Plant Patent
van Opstal

(10) Patent No.: US PP28,472 P2
(45) Date of Patent: Oct. 3, 2017

(54) ***ABELIA* PLANT NAMED 'OPSTAL102'**

(50) Latin Name: *Abelia×grandiflora*
Varietal Denomination: OPSTAL102

(71) Applicant: Ron van Opstal, Zundert (NL)

(72) Inventor: Ron van Opstal, Zundert (NL)

(73) Assignee: RON VAN OPSTAL HOLDING BV, Zundert (NL)

( * ) Notice: Subject to any disclaimer, the term of this patent is extended or adjusted under 35 U.S.C. 154(b) by 128 days.

(21) Appl. No.: 14/756,900

(22) Filed: Oct. 27, 2015

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Abelia×grandiflora* named 'OPSTAL102' that is characterized by its foliage that is irregularly variegated with olive green centers and margins that orange-red to red margins on new growth and mature to green margins with white margins, its numerous blooms that are white in color, and its broadly spreading and densely branched plant habit.

2 Drawing Sheets

Botanical classification: *Abelia×grandiflora.*
Varietal denomination: 'OPSTAL102'.

BACKGROUND OF THE INVENTION

The present invention relates to a new and distinct cultivar of *Abelia×grandiflora* and will be referred to hereafter by its cultivar name, 'OPSTAL102'. 'OPSTAL102' represents a new *Abelia*, an herbaceous perennial grown for landscape use.

The inventor discovered the new cultivar, 'OPSTAL102', as a naturally occurring branch mutation of *Abelia×grandiflora* 'Abelops' (U.S. Plant Pat. No. 20,961) in August 2011 that was growing in a container in Zundert, The Netherlands.

Asexual reproduction of the new cultivar was first accomplished by the inventor by stem cuttings in Zundert, The Netherlands in 2014. It has been determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'OPSTAL102', as unique from all other selections and forms of *Abelia×grandiflora* known to the inventor.

1. 'OPSTAL102' exhibits foliage that is irregularly variegated with olive green centers and margins that orange-red to red margins on new growth and mature to green margins with white margins.
2. 'OPSTAL102' exhibits numerous blooms that are white in color.
3. 'OPSTAL102' exhibits a broadly spreading and densely branched plant habit.

'Abelops', the parent plant of 'OPSTAL102', differs from 'OPSTAL102' in having foliage with margins that mature with a red-orange margin and in having flowers that turn pink-rose in color when mature. 'OPSTAL102' can also be most compared to the cultivar 'Kaleidoscope' (U.S. Plant Pat. No. 16,988) and 'Conti' (U.S. Plant Pat. No 8,472). Both are similar to 'OPSTAL102' in having a broad spreading plant habit. 'Kaleidoscope' differs from 'OPSTAL102' in having leaves that are slightly smaller in size, in having variegated foliage with margins that emerge yellow-green and become flushed with orange, red and yellow in autumn. 'Conti' differs from 'OPSTAL102' in having foliage that is flushed with purple in spring and autumn and in having pale pink flowers.

BRIEF DESCRIPTION OF THE DRAWINGS

The plants and plant parts in the photographs depict a three-year old plant of 'OPSTAL102' as grown outdoors in an unheated greenhouse 33-cm container in Zundert, The Netherlands.

The photograph in FIG. 1 provides a side view of 'OPSTAL102' in bloom.

Figure 1:
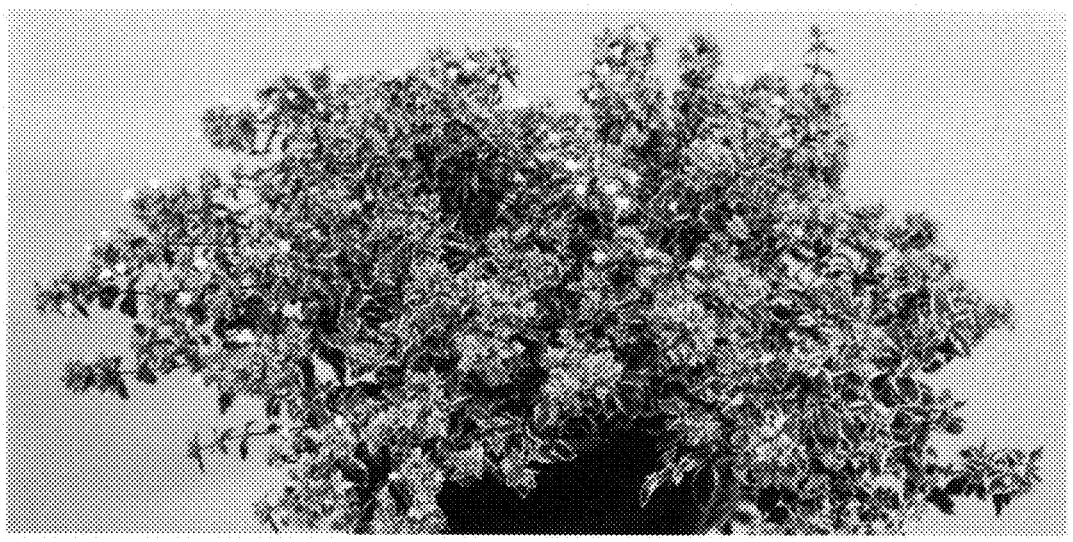
Figure 2:
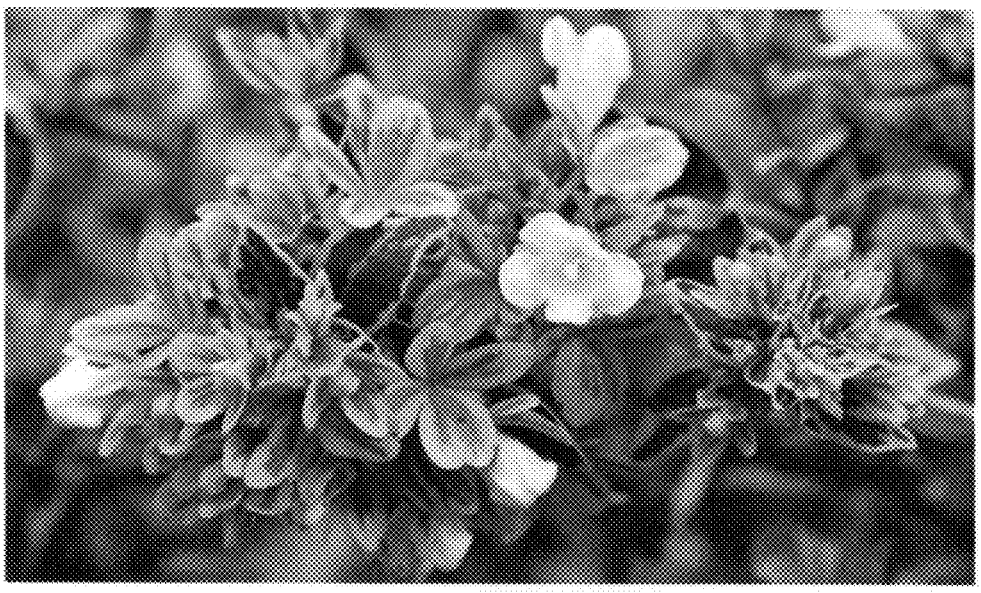

The photograph in FIG. 2 provides a close-up view of a flower of 'OPSTAL102'.

Figure 3:
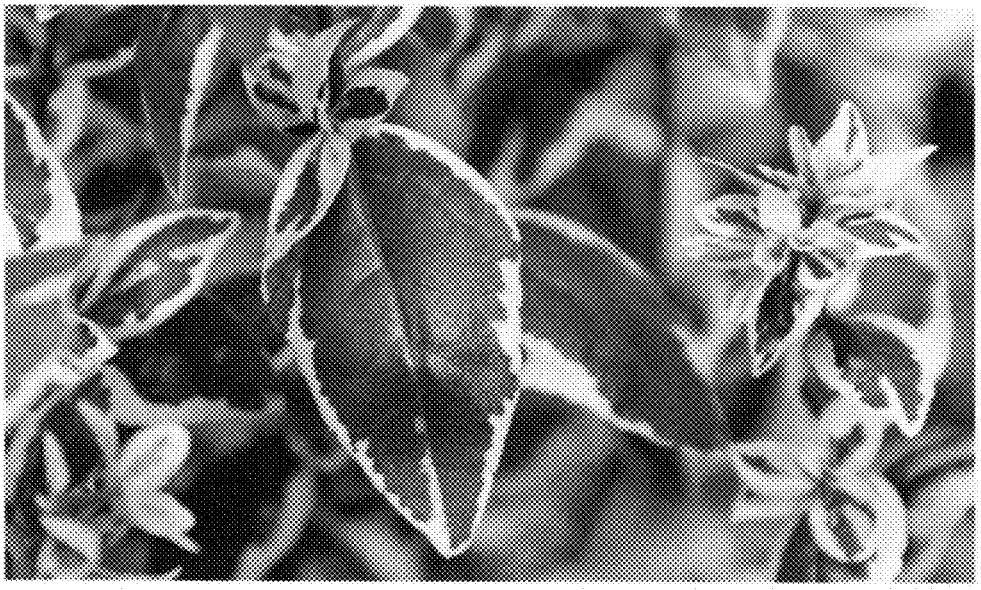

The photograph in FIG. 3 provides a close-up the foliage of 'OPSTAL102'.

The colors in the photographs are as close as possible with the photographic and printing technology utilized and the color values cited in the detailed botanical description accurately describe the colors of the new *Abelia*. The colors in the photographs are as close as possible with the photographic and printing technology utilized. The color values cited in the detailed botanical description accurately describe the colors of the new *Abelia.*

DETAILED BOTANICAL DESCRIPTION

The following is a detailed description of three year-old plants of the new cultivar as grown in an unheated greenhouse in 33-cm containers in Zundert, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Late summer into autumn.

*Plant type*.—Semi-evergeen shrub, observed to be deciduous in The Netherlands.

*Plant habit*.—Broadly spreading.

*Height and spread*.—Average of 30.7 cm in height and 74.5 cm in spread.

*Hardiness*.—Known to be hardy at least to U.S.D.A. Zone 7.

*Diseases and pests*.—Not more susceptible to pests and diseases than other *Abelia* varieties.

*Root description*.—Fine, wiry, and freely branched.

*Propagation*.—Stem division.

*Growth rate*.—Moderate.

*Root development*.—About 12 months to finish a rooted plug in a 13-cm container.

Stem description:

*Stem color*.—Younger branches; upper side of branch 178A, lower side of branch 176B, mature branches; between 199A and N199A.

*Stem size*.—Average of 21.6 cm in length and 2 mm in diameter.

*Stem quantity*.—Average of 102.

*Stem shape*.—Rounded.

*Stem surface*.—Slightly glossy, stems densely covered with very short glandular hairs, average of 0.1 mm in length and too small to measure color.

*Stem aspect*.—Very strong.

*Branching habit*.—Very free branching.

Foliage description:

*Leaf division*.—Single.

*Leaf attachment*.—Petiolate.

*Leaf arrangement*.—Opposite.

*Leaf number*.—Average of 18 (9 pairs).

*Leaf shape*.—Ovate.

*Leaf apex*.—Acute.

*Leaf surface*.—Both surfaces slightly leathery and smooth, upper surface moderately glossy and lower surface matte.

*Leaf base*.—Rounded to very short attenuate.

*Leaf venation*.—Pinnate, upper and lower surface color; 147C.

*Leaf margin*.—Angulate.

*Leaf color*.—Immature upper surface; 147A, irregular margins 35C to 37B to 37C, immature lower surface; 148B, irregular margins 37A, mature (and fall) upper surface; ranging NN137B, irregular margins 150D to 155A, mature (and fall) lower surface; 147B, irregular margins ranging between 155A to 159D.

*Internode*.—Average of 2.4 cm in length.

*Leaf size*.—Average of 3.5 cm in length and 2 cm in width.

*Petioles*.—Average of 2.5 mm in length and 0.15 mm in diameter, both surfaces 147C in color.

Flower description:

*Inflorescence type*.—Terminal compound cymes.

*Inflorescence aspect*.—All directions.

*Inflorescence size*.—Average of 6.8 cm in height and width.

*Flower fragrance*.—Faint, sweet.

*Flower quantity*.—Average of 60 per inflorescence, 6 per lateral stem.

*Flower lastingness*.—Average of 5 days.

*Flower buds*.—Obovate in shape, average of 4 mm in diameter and 9 mm in length, color; 145C.

*Flower aspect*.—All directions.

*Flower shape*.—Campanulate, single.

*Flower size*.—Up to 1.9 cm in depth and 1.4 cm in diameter.

*Petals*.—Average of 5, campanulate, obovate in shape, margin is entire, apex is obtuse, upper (inner) surface is smooth and covered with soft hairs 1 mm in length and NN155D to in color, under (outside) surface smooth and dull, color: upper and lower surfaces when opening; NN155D, upper and lower surfaces when fully open; NN155D average of 1.4 cm in length and 5 mm in width, 57.5% of the lower petals fused.

*Calyx*.—Rotate, average of 7 mm in length and 1.4 cm in diameter, color fades to 39B, center in between 148A and 197A creating an extra ornamental value.

*Sepals*.—5, obovate to elliptic in shape, margin is entire, apex is obtuse, base is cuneate, both surfaces are smooth and dull, color: immature upper surface; 35B, center is 197A, immature lower surface; 38A, center is 197A, mature upper surface; 37A, center is between 148A and 197A, mature lower surface; 37B, center is between 148A and 197A.

*Peduncles*.—Average of 7 mm in length and 1.4 mm in width, strong, color: upper surface; N186C, lower surface; 187A, glabrous surface, average angle of 0° (straight on top of lateral branch), secondary peduncles in an average angle of 60°.

*Pedicels*.—About 1 mm in length and 0.5 mm in width, strong, upper and lower surface 146A in color, glabrous surface, average angle: 0° (straight on top of peduncle), secondary pedicels in an average angle of 50°.

Reproductive organs:

*Gynoecium*.—1 pistil, about 1.25 cm in length, stigma 155A in color, club-shaped, style is about 1.2 cm in length and color is NN155B, base 157D in color, ovary is 146A in color.

*Androcoecium*.—About 4 stamens, anthers are narrow oblong in shape, basifixed, about 1 mm in length and 158D in color, filaments are about 1.1 cm in length and NN155D in color, pollen is moderate in quantity and 156D in color.

*Fruit and seed*.—No fruit or seed have been observed.

It is claimed:

1. A new and distinct cultivar of *Abelia* plant named 'OPSTAL102' as herein illustrated and described.

* * * * *